United States Patent [19]

Dulou et al.

[11] 4,036,884

[45] July 19, 1977

[54] PROCESS FOR THE MANUFACTURE OF A NEW DERIVATIVE OF ALPHA-PINENE AND NEW MEDICAMENTS BASED ON THIS DERIVATIVE

[75] Inventors: Raymond Dulou, Paris; Pierre Magnin, Clermont-Ferrand; Pierre Bechtel, Besancon, all of France

[73] Assignee: So. Ci. Bre., Nanterre, France

[21] Appl. No.: 603,523

[22] Filed: Aug. 11, 1975

Related U.S. Application Data

[63] Continuation of Ser. No. 420,149, Nov. 29, 1973, abandoned, which is a continuation of Ser. No. 222,004, Jan. 31, 1972, abandoned.

[30] Foreign Application Priority Data

Feb. 4, 1971 France .............................. 71.03753

[51] Int. Cl.$^2$ .................... A61K 31/18; C07C 45/00; C07C 49/00
[52] U.S. Cl. ................................. 260/586 G; 424/331
[58] Field of Search .................... 260/586 G; 424/331

[56] References Cited

U.S. PATENT DOCUMENTS 2,773,799  12/1956  Fan ........................................ 424/331

*Primary Examiner*—Frederick E. Waddell
*Attorney, Agent, or Firm*—Larson, Taylor and Hinds

[57] ABSTRACT

The new derivative is 6,6-dimethyl-4-oxo-2-formylbicyclo [3.1.1] hept-2-ene. It is obtained by oxidizing verbenone with selenious anhydride. The new compound has interesting therapeutic properties especially at the level of cellular respiration. Medicaments incorporating the new compound may advantageously be used in a basic treatment of cellular respiratory insufficiency, especially respiratory, cardiac and vascular insufficiencies, severe hepatic insufficiency and phenomena of cellular hypoxia due to aging.

1 Claim, 2 Drawing Figures

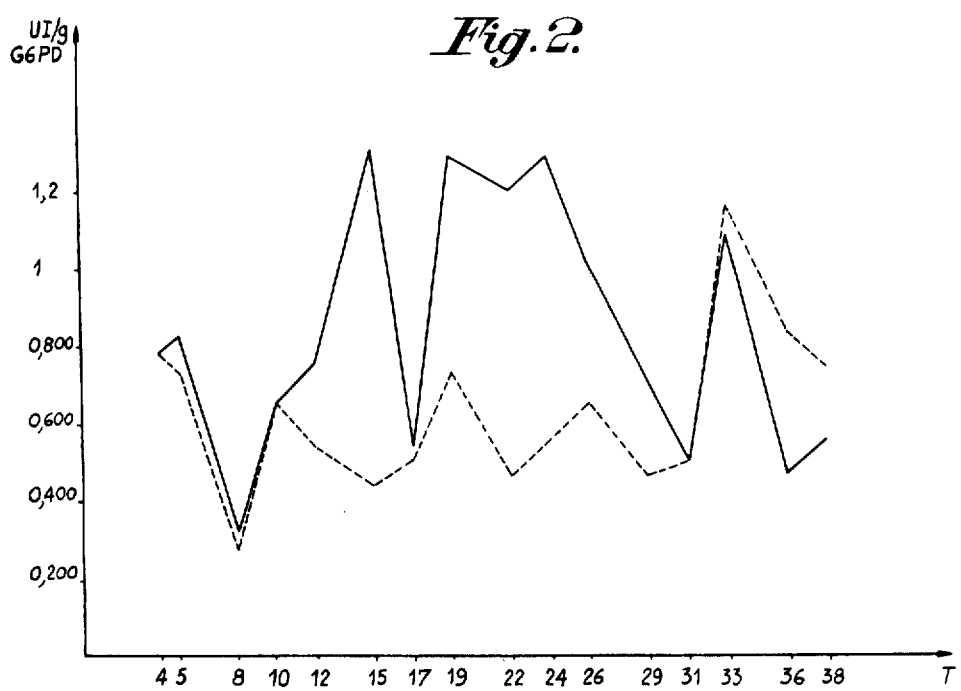

PROCESS FOR THE MANUFACTURE OF A NEW DERIVATIVE OF ALPHA-PINENE AND NEW MEDICAMENTS BASED ON THIS DERIVATIVE

This is a continuation of application Ser. No. 420,149 filed Nov. 29, 1973 (now abandoned) which in turn is a continuation of application Ser. No. 222,004 filed Jan. 31, 1972 (now abandoned).

The present invention relates to a new derivative of α-pinene, and to new medicaments containing this derivative.

The new derivative according to the invention is constituted by 6,6-dimethyl-4-oxo-2-formylbicyclo [3.1.1]hept-2-ene of the formula

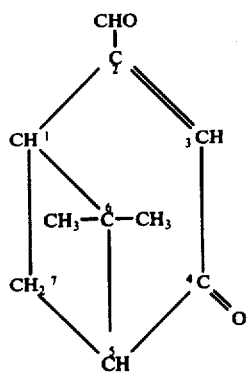

which will hereinafter be called oxomyrtenal.

The invention also relates to the application of oxomyrtenal to the manufacture of medicaments having interesting therapeutic properties, especially at the level of cellular respiration.

The medicaments according to the invention may be advantageously used in the basic treatment of cellular respiratory insufficiency, especially respiratory, cardiac, vascular (arterial and especially coronary, veinous, capillary), severe hepatic insufficiency, and phenomena of cellular hypoxia due to ageing.

The invention concerns also a process for manufactoring oxomyrtenal consisting of oxidising verbenone with selenious anhydride. This reaction is carried out advantageously in the midst of a solvent having a boiling point of the order of 60° to 120° C, maintaining the temperature thereof at about 50° to 60° C during the addition of the selenious anhydride solution to the verbenone solution.

Among particularly suitable solvents for this reaction, there may be mentioned solvents of the alcohol type, especially ethanol, ethereal solvents, pyridine, carbon tetrachloride, etc.

At the end of the addition of the selenious anhydride, the reaction mixture is heated under reflux for several hours. Thus, by using a solvent such as ethanol, the reaction mixture is heated at 80° C for about four hours.

There is given below, an example illustrating the process of preparing oxomyrtenal according to the invention.

EXAMPLE

In a double-necked flask of 500 ml, provided with cooling and a dropping funnel, 100 g of verbenone is dissolved in 100 ml of absolute ethanol. There is then added, drop by drop and with stirring, a solution of 90 g of selenious anhydride in 100 ml of absolute ethanol. During the whole of the addition (about 1 hour), the flask is heated on an oil bath kept at a temperature of 50° to 60° C by a hot plate. Reflux is continued for 4 hours, then the solvent is removed by distillation. The solution thus obtained is filtered, to remove the selenium precipitate, then distilled under reduced pressure. There is then isolated, under a vaccum of 0.1 mm and between 50° and 110° C, 30 to 35 g of a crude brown-red product.

The crude product from the distillation is dissolved in ether and shaken over mercury for 24 hours to remove the selenium remaining in the mixture. Several fractional distillations are then carried out each time carefully placing aside the first fractions and the final heavy fractions.

There is thus isolated 7 g of oxomyrtenal in the form of a yellow oil whose boiling point is, under vaccum 0.1 mm, 90° to 95° C. There can be additionally recovered some further amounts of oxomyrtenal by redistillation of the initial and final fractions.

Oxomyrtenal has an effect with regard to cellular respiration in the sense of an economization of oxygen, as emerges from pharmacological experiments which have been carried out by means of this substance. The effect of oxomyrtenal has therefore been studied on the respiratory of a cellular tissue placed in the presence of an oxidizable substrate, on the phosphorylation reaction of ADP (adenosine diphosphate) into ATP (adenosine triphosphate) at the level of the mitochondrial chain, more particularly on the coupling of this phosphorylation reaction with oxidizing reactions brought into play on the oxidation of a substrate in the respiratory metabolism.

a. Effect of oxomyrtenal on cellular respiratory intensity:

There was studied by manometry the amounts of oxygen consumed, to oxidize a substrate, by control tissues and tissues treated by oxomyrtenal in a hypoxic atmosphere, that is to say an atmosphere of which the oxygen content is less than that of the ambient atmosphere.

Tests carried out were applied to complete homogenates of whole brains of rats, in the presence of glucose as a substrate, in an atmosphere containing 8.5% of oxygen.

For each of the manometric measurements, the brain homogenate is prepared by proceeding in the following manner:

The brains of two rats, previously sacrificed and decapitated are extracted and they are immediately immersed in a buffer previously cooled to 0° C. In view of the very active glycolysis at the level of a brain homogenate and the production of acid metabolites, it is necessary to operate in a completely buffered medium.

It was observed to be particularly advantageous to use for this purpose the buffer described by Lajtha in "Brain Research" pages 186–7, 16, 1969, whose composition is as follows:

| | | | |
|---|---|---|---|
| Na Cl | : | 128 | mM |
| K Cl | : | 5 | mM |
| Ca Cl2 | : | 2.7 | mM |
| Mg SO4 | : | 1.2 | mM |
| Na2 H PO4 | : | 10 | mM (pH 7.4) |
| Tris (hydroxymethyl aminomethane) | : | 100 | mM (pH 7.4) |

Homogenization was effected at 0° C by means of a Potter apparatus (Manometric Technics, Umbreit, Burris and Stauffer, Vol. 1, page 159, 1964 - Burgess Publishing Co - Library of Congress - Washington). An amount of buffer was used so as to have 1 g of total brain in 9 ml of buffer (10% homogenate).

There is utilized by means of a Gilson differential respirometer (pages 102-105 of the last above-indicated reference) the cellular respiration of brain homogenate preparations placed in the presence of glucose.

The preparation subjected to test all contained 2 ml of 10% homogenate. To ten of them were added 300 μg of oxomyrtenal in solution in an inert medium. The six control preparations used were supplemented with corresponding volumes of the Lajtha buffer.

The amount of oxygen consumed by each preparation at 30° C in 2½ hours was measured. There was observed during this period a linear variation of the amounts of oxygen consumed both for the oxomyrtenal preparations and for the control preparations.

In Table I below, there is presented for each type of preparation the average weight of fresh tissue used in these tests and the average amount of oxygen consumed per unit time per gram of fresh tissue. The latter amount is called the respiratory intensity ($QO_2$).

Table I

|  | Average Height of fresh tissue in g | $QO_2$ in $\mu l\, h^{-1}\, g^{-1}$ |
|---|---|---|
| Control preparations | 0.278 | 268 |
| Oxomyrtenal preparations | 0.325 | 194 |

It is clearly apparent from these results that oxomyrtenal produces a lowering of the respiratory intensity of the homogenate concerned. This reduction (average) is 27.6% under the above-indicated experimental conditions.

b. Effect of oxomyrtenal on the phosphorylation reaction of ADP to ATP:

By polargraphy there was studied the development of the oxygen consumption in time of mitochondrial preparations contained in a medium including a defined initial concentration of oxygen when there is added to these mitochondrial preparations an oxidizable substrate, then ADP.

There was used for this purpose mitochondria of rat liver, isolated by centrifugation by means of a Beckmann centrifuge of the Spinco L 50 type. The oxidizable substrate selected was constituted by sodium succinate.

Polarographic measurements were effected by means of a Gilson oxygraph (Methods in Enzymology, Eastbrook R. W. and Pullman N. E., Vol. 10, page 41).

This apparatus, which comprises a vibrating platinum microcathode connected by a saturated KCl bridge to a calomel electrode, enables very sensitive measurements of the variations of oxygen concentration of the mitochrondrial medium concerned.

For each polarographic study, mitochondrial preparations including 1.75 mg of mitochondrial proteins and placed in suspension in a medium having 240 micro M of oxygen and in which the aforesaid polarographic measurements are made, were utilized. The preparations under study received 100 micro M of oxomyrtenal.

Procedure was therefore as follow:

The mitochondria were placed in suspension in the abovesaid medium. There was then noted a very slight consumption of oxygen.

10 μm of succinate was added. There resulted a distinct oxygen consumption to oxidize this substrate. This consumption represents that produced under resting conditions of the mitochondria. It tends to be stabilized after a certain time.

There was then added to the medium 500 nanomoles (nM) of ADP. There was then noted a high oxygen consumption of the mitochondrial medium. The addition of ADP causes an increase in the cellular respiration which results from the transformation of ADP to ATP. This stimulation phenomenon is called respiratory control (CR).

In the case of mitochondrial preparations including oxomyrtenal, the same phenomena as described for the control preparations was observed. However, the oxygen consumption throughout the development of the experiment is distinctly reduced.

In Table II below, there are assembled the results of these polarographic measurements. For each type of preparation, the amount of oxygen consumed in nanoatoms per minute and per milligram of mitochondrial protids was recorded, respectively when succinate is added, and then ADP. There is also indicated the values obtained for each type of mitochondrial preparation for the CR (ratio of the amount of oxygen consumed as a result of the addition of ADP to the amount consumed in the presence of the substrate alone) and for the ratio ADPO (which represents the number of moles of ADP which have been phosphorylated per oxygen atom consumed to oxidize the substrate). ADPO represents therefore the energy recovered by the ADP-ATP phosphorylation to the energy liberated on the oxidation of the substrate.

Table II

|  | Succinate | | ADP | | | |
|---|---|---|---|---|---|---|
|  | Amount of oxygen in $n\text{-}at.mn^{-1}$ | $QO_2$ n-at. $mn^{-1}mg^{-1}$ | Amount of oxygen in $n\text{-}at.mn^{-1}$ | $QO_2$ n-at. $mn^{-1}mg^{-1}$ | C R | ADP/0 |
| Control preparations | 256 | 146 | 425 | 242 | 1.7 | 2 |
| Oxomyrtenal preparations | 128 | 73 | 262 | 150 | 2.05 | 1.71 |

The oxamination of the results assembled in the above Tables shows that in the presence of oxomyrtenal the respiratory intensity of the mitochondrial chain is distinctly reduced, and that this reduction is not accompanied by an inhibition of the phosphorylating oxidation processes.

The values of the CR and of the ratio ADPO remain in fact practically unchanged with respect to the control. The mitochondrial chain remains therefore capable, in the case of need by the organism, of increasing its respiratory intensity to enable transformation of ADP- →ATP. Moreover, the recovery of the energy freed on the oxidation of the succinate substrate is effected practically in the same ratio for a mitochondrial preparation whether treated or not with oxomyrtenal.

c. Survival of animals in a hypoxic atmosphere

Fifty-five mice receive by intraperitoneal injection doses of oxomyrtenal at the rate of 1 mg per day for four days and 0.5 mg the fifth day. Each of them is introduced a half hour after the last injection into a cage under a hypoxic atmosphere with 5% of oxygen. Fifty-five control mice underwent the same treatment. The durations of survival of these mice was measured.

The average duration of survival of the control mice is 138 seconds, that of the animals previously treated with oxomyrtenal, 257 seconds.

It was also noted that none of the control group of animals survived more than three minutes. The duration of survival of certain of the mice previously treated with oxomyrtenal reached 20 minutes.

These results enable it to be concluded that oxomyrtenal favors the metabolic cellular adaptation to hypoxia.

d. Action of oxomyrtenal on the cellular energy metabolism

Nice received daily by intraperitoneal injection two doses of 0.5 mg of oxomyrtenal, namely one mg of oxomyrtenal per day per animal. Control mice were kept under the same ecological conditions as the treated mice.

There were sacrificed, after increasing intervals of time from the beginning of the treatment, mice from the treated group and from the control group. Each time the livers and the brains of the sacrificed animals were removed and on these organs doses of lacto-deshydrogenase (LDH) and 6-glucose-phosphate-deshydrogenase (G6PD) were administered.

It will be recalled that these enzymes play an important role at the level of cellular respiration. LDH catalyses the deshydrogenation of lactic acid into pyruvic acid and G6PD is the first enzyme of the catabolic route of glucose (pentose-phosphate route) and plays an important role in the maintenance of the NADP (nicotinamide-adenine-dinucleotide-phosphate) in its hydrogenated form NADP $H_2$. This increase can also show an increase in the synthesis of the riboses, and consequently, of the nucleic acids.

The curves of FIGS. 1 and 2 respectively are representative of the results obtained, for the two enzymes. They show the variations in the enzymatic activities per gram of the fresh organ, expressed in UI/g, as a function of time T, expressed in days of treatment before sacrifice of the animals concerned, the curves in full lines relating to treated animals, those in interrupted lines the controls (1 UI/g of enzyme catalyzed at the temperature 30° C, the transformation of a micromole of substrate constituted per minute).

There was observed in the treated animals an LDH activity at the level of the liver, always very high, at least for 38 days, as in the control animals (FIG. 1).

In the same way the G6PD activity in the treated animals is distinctly increased at the level of the liver with respect to that of the control animals, between the fifteenth and the thirty-first days (FIG. 2).

On the contrary no difference was noted at the brain level. The other enzymatic activities are practically unmodified.

The increases in the syntheses of LDH and of G6PD are manifested respectively by the continuation of an energy producing metabolism by stimulation of glycolysis (by the Mendel-Meyerof route) and a reinforcement of proteic syntheses.

These effects can be considered as the consequence of the reduction in the respiratory intensity already noted in the course of experiments carrid out in virto and interpreted as being of a nature to favor the metabolic cellular adaptation to hypoxia.

The medicaments according to the invention are of great interest for the treatment in depth of cellular respiratory insufficiency, especially in the following indications: respiratory, cardiac, vascular (arterial and especially coronary, venous and capillary) insufficiencies, severe hepatic insuffiency, phenomena of cellular hypoxia due to aging.

These medicaments can be administered by the parenteral, oral and rectal route.

The daily posologic dose of active substance can be of the order of 20 to 150 mg (in 1 to 4 administrations) for application by the parenteral route, from 50 to 800 mg (in 1 to 8 administrations) by the oral route, and from 100 to 800 mg (in 1 to 4 administrations) by the rectal route.

Administration by the parenteral route is, for example, effected in the form of injectable solutions containing, in combination with the oxomyrtenal, 95° ethanol, sodium laurylsulfate, a non-ionic emulsifier and an isotonic aqueous excipient buffered to pH 4.5.

For the administration by the rectal route, suppositories are used containing, in combination with the oxomyrtenal, advantageously semi-synthetic glycerides.

As is self-evident and as emerges already from the foregoing, the invention is in no way limited to those of its types of application, nor to those of its embodiments of its various parts, which have been more especially envisaged; it encompasses, on the contrary, all modifications.

We claim:
1. The novel chemical compound: 6,6-dimethyl-4-oxo-2-formylbicyclo [3.1.1]hept-2-ene of the formula:

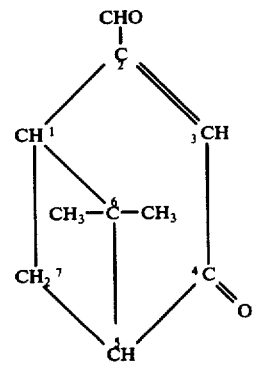

* * * * *